United States Patent
Benner et al.

(10) Patent No.: US 7,794,936 B1
(45) Date of Patent: Sep. 14, 2010

(54) USING THYMIDINE ANALOGS TO IMPROVE REPLICATION IN AN EXPANDED GENETIC ALPHABET

(76) Inventors: Steven Albert Benner, 1501 NW. 68th Ter., Gainesville, FL (US) 32605-4147; Albert Michael Sismour, 85 Hancock St., Apt. 7, Cambridge, MA (US) 02139

( * ) Notice: Subject to any disclaimer, the term of this patent is extended or adjusted under 35 U.S.C. 154(b) by 534 days.

(21) Appl. No.: 11/541,295

(22) Filed: Sep. 29, 2006

(51) Int. Cl.
 *C12Q 1/68* (2006.01)
(52) U.S. Cl. .................. 435/6; 536/22.1; 536/24.33
(58) Field of Classification Search .................. None
 See application file for complete search history.

(56) References Cited

U.S. PATENT DOCUMENTS 6,977,161 B2 * 12/2005 Grenier et al. ............. 435/91.2

OTHER PUBLICATIONS

Sismour et al. Nucleic Acids Research vol. 32:728-735. 2004.*
Horlacher, J., Hottiger, M., Podust, V. N., Huebscher, U., Benner, S. A. (1995) Recognition by viral and cellular DNA polymerases of nucleosides bearing bases with non-standard hydrogen bonding patterns. Proc. Natl. Acad. Sci. USA 92, 6329-6333.
Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. Nucleic Acids. Res.32, 2, 728-735.
Sismour, A. M., Benner, S. A. (2005) The use of thymidine analogs to improve the replication of an extra DNA base pair. A synthetic biological system. Nucleic Acids Res. 33, 17, 5640-5646.
Yang, Z., Hutter, D., Sheng, P., Sismour, A. M., Benner, S. A, (2006) Artificially expanded genetic information system: A new base pair with an alternative hydrogen bonding pattern. Nucleic Acids Res. 34, 21, 6095-6101.
Yang, Z., Sismour, A. M., Sheng, P., Puskar, N. L., Benner, S. A. (2007) Enzymatic incorporation of a third nucleobase pair. Nucleic Acids Res. 35, 13, 4238-4249.
Michiko Kimoto, Rie Kawai, Tsuneo Mitsui, Shigeyuki Yokoyama, Ichiro Hirao An unnatural base pair system for efficient PCR amplification and functionalization of DNA molecules Nucleic Acids Research, 2009, vol. 37, No. 2 e14.
Chen, F., Gaucher, E. A., Leal, N. A., Hutter, D., Havemann, S. A., Govindarajan, S., Ortlund, E. A., Benner, S. A. (2010) Reconstructed evolutionary adaptive paths give polymerases accepting reversible terminators for sequencing and SNP detection. Proc. Natl. Acad. Sci. USA 107, 5,1948-1953.

\* cited by examiner

*Primary Examiner*—Heather Calamita

(57) ABSTRACT

This invention relates to nucleoside, nucleotide, and oligonucleotide analogs that incorporate non-standard nucleobase analogs, those that present a pattern of hydrogen bonds to a paired nucleobase analog in a complementary strand that is different from the pattern presented by adenine, guanine, cytosine, and thymine. Most specifically, this invention discloses and claims processes for amplifying nucleic acid analogs containing non-standard nucleobases using polymerase chain reactions, and combinations of non-standard nucleobases, analogs of standard nucleotides, and enzymes that perform this amplification. Most specifically, this invention is for the use of 2-thiothymidine triphosphate (2-thioTTP) instead of thymidine triphosphate in a six letter polymerase chain reaction that includes 2'-deoxyadenosine triphosphate, 2'-deoxyguanosine triphosphate, 2'-deoxycytidine triphosphate, 2'-deoxy-iso-guanosine triphosphate, and 2'-deoxy-iso-cytidine triphosphate, as well as their forms that contain side chain modifications. Because of the size and hydrogen bonding properties of the sulfur unit in 2-thioT, 2-thioT does not mispair effectively with the minor tautomer of isoG. This permits the PCR amplification of a six letter artificially expanded genetic information system, we examined the relative rates of misincorporation of 2-thioTTP and TTP opposite isoG using affinity electrophoresis with a fidelity-per-round of ca. 98%. The analogous PCR employing TTP has a fidelity-per-round of only ca. 93%. Therefore, this invention represents the first example of a six letter artificial genetic system that is amplifiable by a thermostable polymerase, and capable of Darwinian evolution.

8 Claims, 6 Drawing Sheets

USING THYMIDINE ANALOGS TO IMPROVE REPLICATION IN AN EXPANDED GENETIC ALPHABET

STATEMENT OF RIGHTS TO INVENTIONS MADE UNDER FEDERALLY-SPONSORED RESEARCH

This invention was made with government support under CHE0434507 awarded by the National Science Foundation's Center for Chemical Bonding. The government has certain rights in the invention

CROSS REFERENCE TO RELATED APPLICATIONS

None

NAMES OF THE PARTIES TO A JOINT RESEARCH AGREEMENT

Not applicable.

INCORPORATION-BY-REFERENCE OF MATERIAL SUBMITTED ON A DISC

None.

FIELD

This invention relates to the field of nucleic acid chemistry, more specifically to the field of compositions and processes that can be used to amplify nucleic acid analogs. More specifically, this invention relates to compositions that allow the artificial selection based on artificial genetic systems.

BACKGROUND

Artificially expanded genetic information systems, often known by the acronym AEGIS, have been widely sought [Sis04][Joh04][Liu04][Hen04][Ben04][Ben05], including in the patent literature (U.S. Pat. No. 5,432,272, for "Method for incorporating into a DNA or RNA oligonucleotide using nucleotides bearing heterocyclic bases"; U.S. Pat. No. 6,001,983, for "Oligonucleotides with non-standard bases and methods for preparing same"); U.S. Pat. No. 6,037,120, for "Recognition of oligonucleotides containing non-standard base pairs"; U.S. Pat. No. 6,140,496, for "Precursors for deoxyribonucleotides containing non-standard nucleosides"; and U.S. Pat. No. 5,965,364, for "Method for selecting functional deoxyribonucleotide derivatives"). They are also being mentioned in the popular press [Bal04][Gib04]. A variety of partial solutions to this problem have been reported [Sis04][Del03][Tae01][Hik05].

Without involvement of polymerases, six letter expanded genetic alphabets support clinical assays today that quantitate (through simple Watson-Crick binding) the levels of HIV, hepatitis B and hepatitis C viruses in infected patients; an estimated 400,000 individuals annually benefit in the management of their health care using AEGIS [Elb04a][Elb04b].

The enzymatic synthesis of DNA containing AEGIS components, however, remains problematic [Hor95][Swi93][Swi89], especially when it concerns the amplification of DNA using the polymerase chain reaction. These difficulties are due, in part, to the highly evolved specificity of natural DNA polymerases. This evolution allows them to accept the standard A, G, T, C, but little else with efficiency and high fidelity [Goo93][Mor00][Tab95][Mey04].

Sismour et al. [Sis04] recently reported the PCR amplification of DNA containing a pair between 2,4-diaminopyrimidine and xanthine (called the pyDAD:puADA base pair, because the pyrimidine implements the hydrogen bond Donor-Acceptor-Donor hydrogen bond pattern, from the major groove to the minor groove, complementary to the Acceptor-Donor-Acceptor pattern implemented by the purine xanthine). This was achieved using a double mutant of the reverse transcriptase from human immunodeficiency virus (HIV) I that was obtained by a combination of in clinico selection and rational design. This mutant amplified an oligonucleotide containing a single pyDAD over five rounds of PCR with an overall fidelity (per round) of >99% for the pyDAD:puADA base pair. This process has only narrow utility, however, as the reverse transcriptase is not stable to heating, and therefore must be added anew after each heat cycle.

A second PCR amplification of DNA containing an iso-C:iso-G (pyAAD:puDDA) nucleobase pair was achieved for several dozen rounds of amplification [Jooh04] using a fragment of DNA polymerase I from *Thermus aquaticus* that does not have an 5'→3' exonuclease domain, with a fidelity of only ~96% per round. The *T. aquaticus* polymerase is stable against thermal denaturation. A fidelity of less than 98% per round is not adequate for most practical applications, including using the six letter alphabet as part of an in vitro selection system.

Similar problems are encountered where steric complementarity is used as the basis for nucleobase pairing specificity [Mor97][Ber00][Hir04].

The loss of fidelity in the system reported by [Joh04] is most likely due to a mispairing of TTP opposite isoG. This mispairing was found in earlier work by Switzer et al. [Swi93]. It is also expected, given the long known fact that isoG has a minor tautomeric form that is complementary to T, and present in aqueous solution to the extent of ca. 10%.

DETAILED DESCRIPTION OF THE INVENTION

Thiones (the C=S unit, as in thioT) do not serve well as hydrogen bond acceptors, either in solution or in Watson-Crick pairing [Lez67][Dar73][Vor74][Rac77]. For example, while a nucleobase pair between 2-thioT and adenine contributes to duplex stability (as measured by ΔG) as well as a pair between T and A, a nucleobase pair between 2-thioT and 2-aminoadenine destabilizes the duplex by 0.8 kcal/mol (corresponding to a 2.4° C. decrease in $T_m$ in a 20 nucleotide duplex) [Kut96]. This destabilization has been attributed to the increased steric crowding within the C=S H—NH— contact in the minor groove of the double helix.

Figure 1:
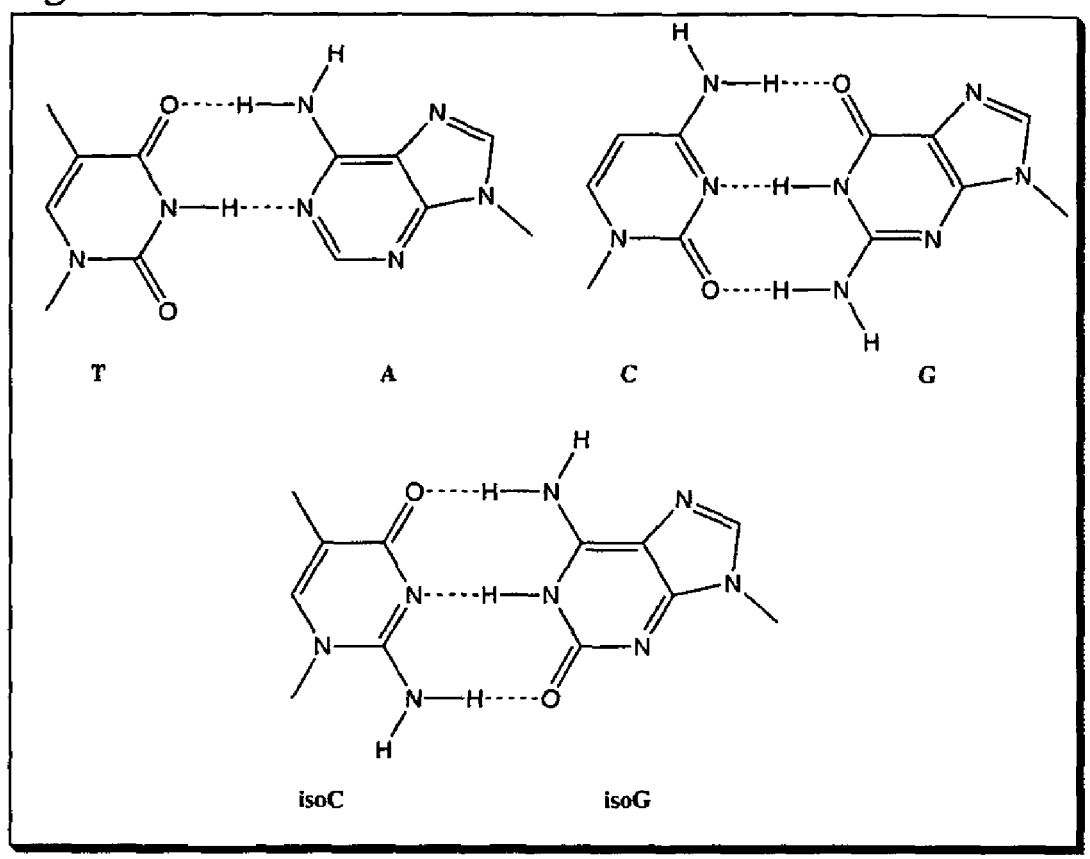
FIG. 1. Artificially expanded genetic information system used in this study.
Figure 2:
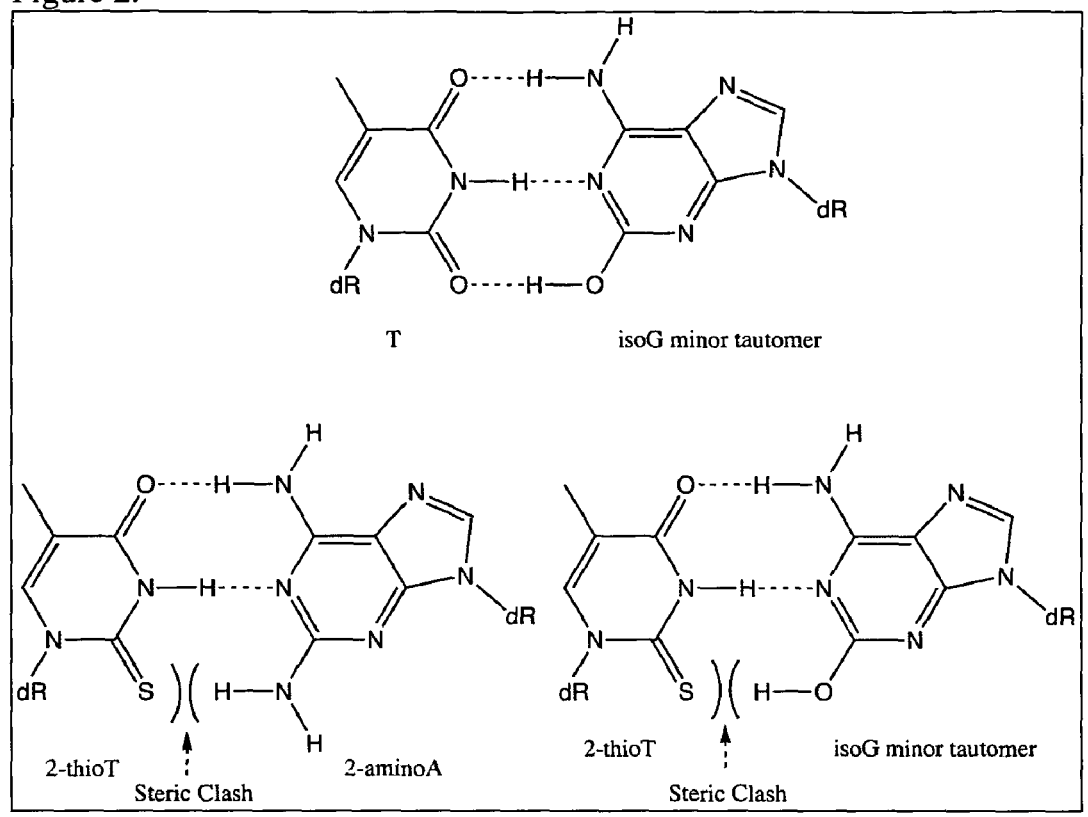
FIG. 2. Steric exclusion of 2-thioT-isoG base pair. Shown is the mispair between thymidine (T) and the minor tautomer of isoG, resulting in replication infidelity. Shown as well is the pair between 2-thiothymidine (2-thioT) and 2-aminoadenine, showing a steric clash in the minor-groove. Similarly, a steric clash between 2-thiol and the minor tautomer of isoG is expected to inhibit formation of this mispair.

The minor tautomer of isoG, responsible for its mispairing with thymidine, delivers a HO-group to the minor groove in a position that allows the H of the HO-group to form a hydrogen bond with the minor groove C=O of standard thymidine. The inventive concept, therefore, was to replace the C=O at position 2 of standard thymine by a C=S thione unit, that is, by replacing thymidine by 2-thiothymidine. This led to the prediction that the 2-thiothymidine-isoG (minor tautomer) nucleobase pair should be disfavored relative to the thymidine-isoG (minor tautomer) nucleobase pair in a polymerase active site as well (FIG. 2).

This invention discloses and claims processes for amplifying nucleic acid analogs containing non-standard nucleobases using polymerase chain reactions, and combinations of non-standard nucleobases, analogs of standard nucleotides, and enzymes that perform this amplification. Most specifically, this invention is for the use of 2-thiothymidine triphosphate (2-thioTTP) instead of thymidine triphosphate in a six letter polymerase chain reaction that includes 2'-deoxyadenosine triphosphate, 2'-deoxyguanosine triphosphate, 2'-deoxycytidine triphosphate, 2'-deoxy-iso-guanosine triphosphate, and 2'-deoxy-iso-cytidine triphosphate 2'-deoxyadenosine triphosphate, as well as their modified forms. Experimentally, we expected that any DNA polymerase from evolutionary Family A or Family B will work. The presently preferred polymerases are from Family A. The most preferred polymerase is the "Klenow" fragment of Taq polymerase. These polymerases do not discriminate well against the T-isoG pair, should discriminate well against the 2-thioT:isoG pair. Thus, we predicted that the PCR amplification of a six letter artificially expanded genetic information system of the instant invention should have a useful fidelity, of at least 98% per round.

Example 1

Oligonucleotides and Enzymes

Oligonucleotides (Table 1) were synthesized by Integrated DNA Technologies (Coralville, Iowa) and purified by polyacrylamide gel electrophoresis (10-20%).

Table 1. Oligonucleotides used in this study.

T-1 5'-GTC TTC GTG TCA CG(isoG) CCA TAG TGA GTC GTA TTA CGC-3'

T-2 5'-GCG AAT TAA CCC TCA CTA AAG TAC G(isoG)T CGT CTA TAG TGA GTC GTA TTA CGC-3'

T-3 5'-GCG AAT TAA CCC TCA CTA AAG TAC GAT CGT CTA TAG TGA GTC GTA TTA CGC-3'

P-1 5'-GCG TAA TAC GAC TCA CTA T-3'

P-2f 5'-GCG TAA TAC GAC TCA CTA TAG-3'

P-2r 5'-GCG AAT TAA CCC TCA CTA AAG-3'

The "Klenow" fragment of Taq polymerase (Titanuim™ Taq) was purchased from BD Biosciences (Mountain View, Calif.). As Titanium™ Taq is a "hot start" enzyme, the enzyme was heated to 95° C. for 2 minutes, followed by rapid cooling to ambient temperature prior to any primer extension reactions. Similarly, all polymerase chain reactions included an initial 2 minute 95° C. denaturation cycle.

Primer Extension Reactions

In a typical primer extension reaction (25 μL total volume), 5'-$^{32}$P labeled primer (P-1, 25 pmol) and template (T-1, 30 pmol) were mixed with buffer (10 mM bis-trispropane-HCl pH 9.1, 5 mM $MgCl_2$, 40 mM potassium acetate, 0.1 mg/ml bovine serum albumin), heated (95° C., 5 min), and cooled to room temperature over 1 hour. Polymerase (1 unit) was added, and the mixture again heated (72° C., 10 sec). Each PCR was initiated by adding the appropriate dNTPs (100 μM final concentration). Aliquots (2 μL) were removed from the mixture at time intervals, diluted into a PAGE loading/quench buffer (2 μL, 20 mM EDTA in formamide), heated (95° C., 5 min) and resolved by electrophoresis using a 20% PAGE (7 M urea). The gel was analyzed by phosphorimager. To enhance reproducibility, master mixes of the primer/template in buffer were prepared in large scale (100 μL).

Nucleotide Competition Reactions

Single turnover primer extension reactions were performed by annealing 5'-$^{32}$P labeled primer (P-2f, 1 pmol) and template (T-2 or T-3, 1 pmol) in the appropriate buffer described above. Polymerase (1 pmol) was added, and the mixture was heated (72° C., 10 sec). The reaction was initiated by adding isoCTP (100 μM) and either 2-thioTTP (100 μM) or TTP (100 μM) in the presence of unlabeled trap DNA (P-2f, 100 pmol, T-2, 100 pmol). The reaction was quenched (20 mM EDTA in HCONH$_2$) after 20 sec, and the samples resolved by 20% PAGE (7 M urea) containing p-acrylamidophenylmercury chloride (APM, 1 μg/mL). This permitted the separation of oligonucleotides containing thiothymidine (which ran slower) from those that did not. APM was synthesized as described [Igl88].

PCR Amplification and Fidelity Assay

For each 6-letter nucleotide system investigated, seven parallel PCR mixtures were cycled (30 rounds, 95° C. for 45 sec. then 45° C. for 45 sec. then 72° C. for 1.5 min) with the same amounts of primers P-2f ($^{32}$P labeled) and P-2r (1 pmol; 6×10$^{11}$ molecules) and varying concentrations of template T2. These were obtained by 10 fold serial dilutions (from 6×10$^4$-6×10$^{10}$ molecules per reaction). As each 10 fold dilution in template was equivalent to ca. 3.3 rounds of amplification, the fidelity of the isoC:isoG replication could be monitored on a round-by-round basis, with each amplicon requiring a different number of exponential amplifications to consume the primers (Table 2.)

Following amplification, the mixtures were treated with an equal volume of acetic acid (0.1 mM), and heated (95° C., 30 min), a procedure that depyrimidinylates the iso-cytidines that have been incorporated. The tubes were then opened, and the solvents removed by evaporation at atmospheric pressure. Two volumes of NH$_4$OH (0.1 mM) were added and incubation continued (95° C., 5 min). This cleaves the product DNA strands at sites where isoC had been present. The NH$_4$OH was allowed to evaporate, and the mixtures diluted in 2 volumes of gel loading buffer (98% formamide, 10 mM EDTA, 1 mg/mL bromophenol blue, 1 mg/mL xylene cyanol FF) and analyzed by denaturing PAGE (17%). Quantitation of the band generated by cleavage at isoC vs. full-length product (not containing isoC) provided a measure of the fidelity of isoC and isoG replication.

Amplicons testing the substitution of 2-thioTTP for TTP in a PCR were generated as above, using primers P-2f and P-2r (1 pmol each), template T-3 (6×10$^4$ molecules), and either all four natural dNTPs (100 μM each) or by substituting 2-thioTTP for TTP.

Data Analysis

To estimate the fidelity per round of the PCRs, the percent of product containing isoC, as determined by the cleavage assay, was plotted versus the number of doublings required to consume all of the added primer. The number of product molecules generated in a perfect PCR is equal to $N=n\ 2^r$ (equation 1), where n equals the number of template molecules, N equals the number of product molecules, and r equals the number of rounds of perfect doubling required to use all primer molecules. Similarly, the number of product molecules containing isoC is equal to $N_{iC}=n\ (1+f)^r$ (equation 2), where f is the fidelity per round. The percentage of the PCR product containing the isoC:isoG base pair is equal to $N/N_{iC}$, which simplifies to $(\frac{1}{2}+f/2)^r$. Data from the PCR amplifications were graphed and fit to the equation $y=100\ (1+f)^r$ using the program Kaleidagraph Version 3.5; Synergy Software, Reading, Pa.), where X is the number of doublings (i.e. PCR rounds) as calculated in Table 2; y is the percent cleaved product from each reaction.

Table 2. PCR amplicons. Each amplicon was cycled for 30 PCR rounds. Each reaction had the same amounts of primer, but different amounts of template, and therefore different ratios of primer to template. The number of perfect doublings required to convert all primer to product is dependent on the primer to template ratio (amplification), and is equal to the number of rounds of PCR (under ideal conditions) needed to consume the primer. Doublings=$\log_2$ (# primer molecules/# template molecules).

| Template molecules | 6 × 10$^{10}$ | 6 × 10$^9$ | 6 × 10$^8$ | 6 × 10$^7$ | 6 × 10$^6$ | 6 × 10$^5$ | 6 × 10$^4$ |
|---|---|---|---|---|---|---|---|
| Primer molecules | 6 × 10$^{11}$ | 6 × 10$^{11}$ | 6 × 10$^{11}$ | 6 × 10$^{11}$ | 6 × 10$^{11}$ | 6 × 10$^{11}$ | 6 × 10$^{11}$ |
| Amplification | 10 | 10$^2$ | 10$^3$ | 10$^4$ | 10$^5$ | 10$^6$ | 10$^7$ |
| Doublings (PCR rounds) | 3.32 | 6.64 | 9.97 | 13.29 | 16.61 | 19.93 | 23.25 |

Primer Extension Studies

Running-start primer extension reactions were performed with KlenTaq to determine the ability of the enzyme to incorporate either TTP or 2-thioTTP opposite isoG. For each reaction, the polymerase was challenged to misincorporate the respective triphosphate opposite the isoG residue at position 26 in the template (T-1), 3 nucleotides downstream of the primer (Pf-1) terminus. Reactions were run in parallel, one containing dGTP and TTP, one containing dGTP and 2-thioTTP, one containing dGTP and isoCTP (positive control), and one containing only dGTP (negative control). Aliquots of each reaction were quenched at various times and analyzed by PAGE on a 20% polyacrylamide gel.

In running-start primer extension reactions (FIG. 3), KlenTaq polymerase incorporated all 3 dNTPs tested (isoCTP, TTP, 2-thioTTP) opposite an isoG in the template, with isoCTP incorporated most efficiently, followed by TTP and 2-thioTTP. It is noteworthy that after one and three minutes of incubation, the polymerase incorporated approximately 2 fold more isoCTP than TTP opposite isoG.

This result illustrates the known nonspecificity of polymerases challenged with a template containing isoG. Most polymerases also incorporate T as well as isoC opposite isoG, either via a wobble base pair or, more likely, opposite the minor tautomer of isoG that is complementary (in the Watson-Crick hydrogen bonding sense) to T [Rob98].

Figure 3:
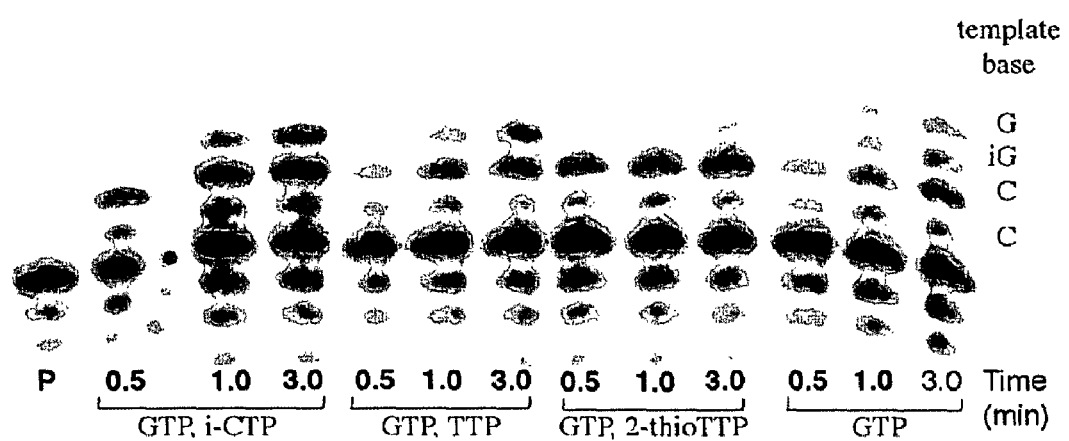
FIG. 3. Primer extension reactions comparing 2-thioTTP and TTP incorporation opposite isoG. Taq polymerase was incubated with template (T-1), primer (P-1), dGTP, and either isoCTP, TTP, or 2-thioTTP at 72° C. Time points taken at 0.5, 1.0, and 3.0 minutes show extension up to the template isoG (by incorporation of two dGTPs), and incorporation of the dNTP of interest (isoCTP, TTP, or 2-thioTTP) opposite the isoG. The data suggest that TTP is more readily incorporated opposite isoG than is 2-thioTTP.

These data also show that 2-thioTTP was misincorporated very little opposite isoG in the 0.5 and 1 min incubations. After 3 min, misincorporation gave rise to a more obvious band (FIG. 3). This establishes that 2-thioTTP is misincorporated opposite isoG to a much lesser extent than is TTP. This is especially true at incubation times relevant for a typical PCR elongation step (for DNA $\leq$2 Kb) of between 45 and 90 seconds.

In two parallel reactions, one containing equal concentrations of 2-thioTTP and TTP, and one containing equal concentrations of 2-thioTTP and isoCTP, KlenTaq polymerase was challenged to choose a nucleotide to incorporate opposite isoG. Affinity electrophoresis on a polyacrylamide gel (20%) containing p-acrylamidophenylmercury chloride (APM, 10 µg/mL) was used to separate those products extended with a 2-thioT from those extended with a non sulfur-containing dNTP (isoCTP, or TTP) [Igl88]. The gel was analyzed via radioimaging.

Figure 4:
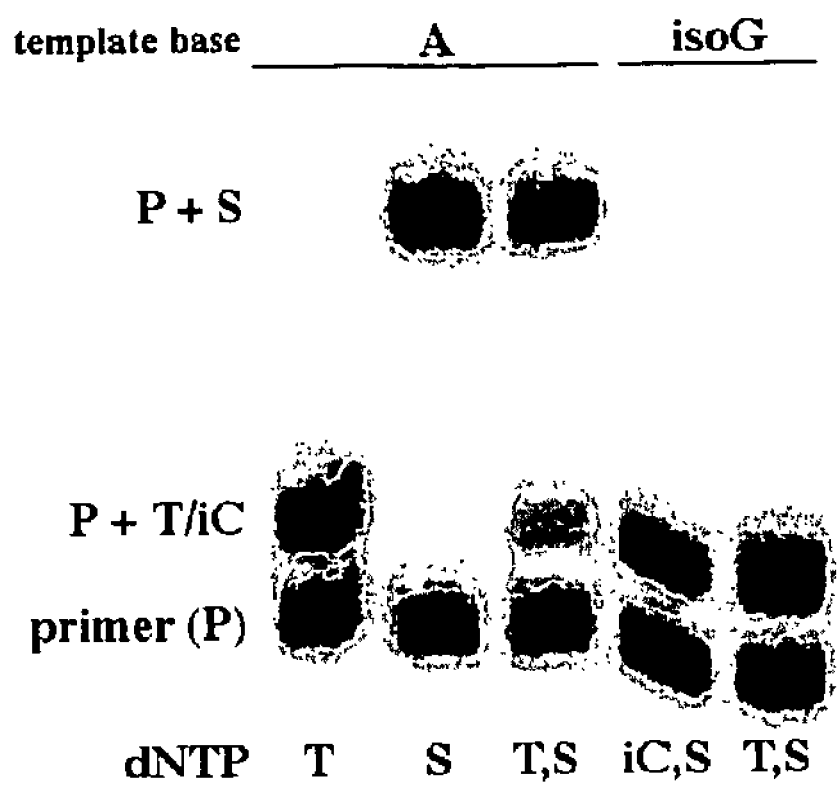
FIG. 4. Direct competition studies opposite isoG. The ratio of incorporation of 2-thioTTP to isoCTP or TTP was tested in a single-turnover primer extension reaction by incubating Taq polymerase with primer-template (primer P-2f, template T-2), and equal concentrations of 2-thioTTP and either TTP or isoCTP. Control reactions challenged the polymerase to extend a primer-template with adenosine replacing the non-natural isoG (primer P-2, template T-3) in the presence of TTP, 2-thioTTP, or both TTP and 2-thioTTP. Reaction products were separated by denaturing PAGE on a 20% gel containing APM, allowing for the separation of products containing 2-thiol from those that do not (see text for details). These data show that while 2-thioTTP is preferred over TTP for incorporation opposite adenosine, both isoCTP and TTP are preferred over 2-thioTTP for incorporation opposite isoG. S indicates 2-thioTTP, iC indicates isoCTP, P+T/iC is the product from the polymerase adding a single TTP or isoCTP to the primer (P), while product resulting from the addition of a single 2-thioTTP to the primer is annotated as P+S.

FIG. 4 shows the results of the direct competition experiments, wherein the DNA containing 2-thioT migrates at a slower rate than a typical oligonucleotide due to the interaction of its thiol with the mercury in the APM. It is observed that when placed in direct competition for incorporation, the polymerase incorporates either isoCTP or TTP opposite isoG, with less than 1% of the extended product resulting from incorporation of 2-thioTTP. Also notable is the observation that Taq polymerase prefers 2-thioTTP over TTP as a substrate for incorporation opposite adenosine. This unexpected result was not observed for Family B polymerases (data not shown).

PCR Amplification

After showing that 2-thioTTP is misincorporated less frequently than TTP opposite isoG residues, we then established that 2-thioTTP works in a PCR amplification. For this purpose, replicate polymerase chain reactions with KlenTaq polymerase were performed using the PCR replicon consisting of primers P-2f and P-2r and template T-3. Three reactions were run in parallel, one containing the four natural dNTPs (positive control), one containing dCTP, dGTP, dATP, and 2-thioTTP, and one without TTP (negative control). Each amplification was cycled for 30 rounds, and the products were analyzed by electrophoresis on a 2% agarose gel.

Figure 5:
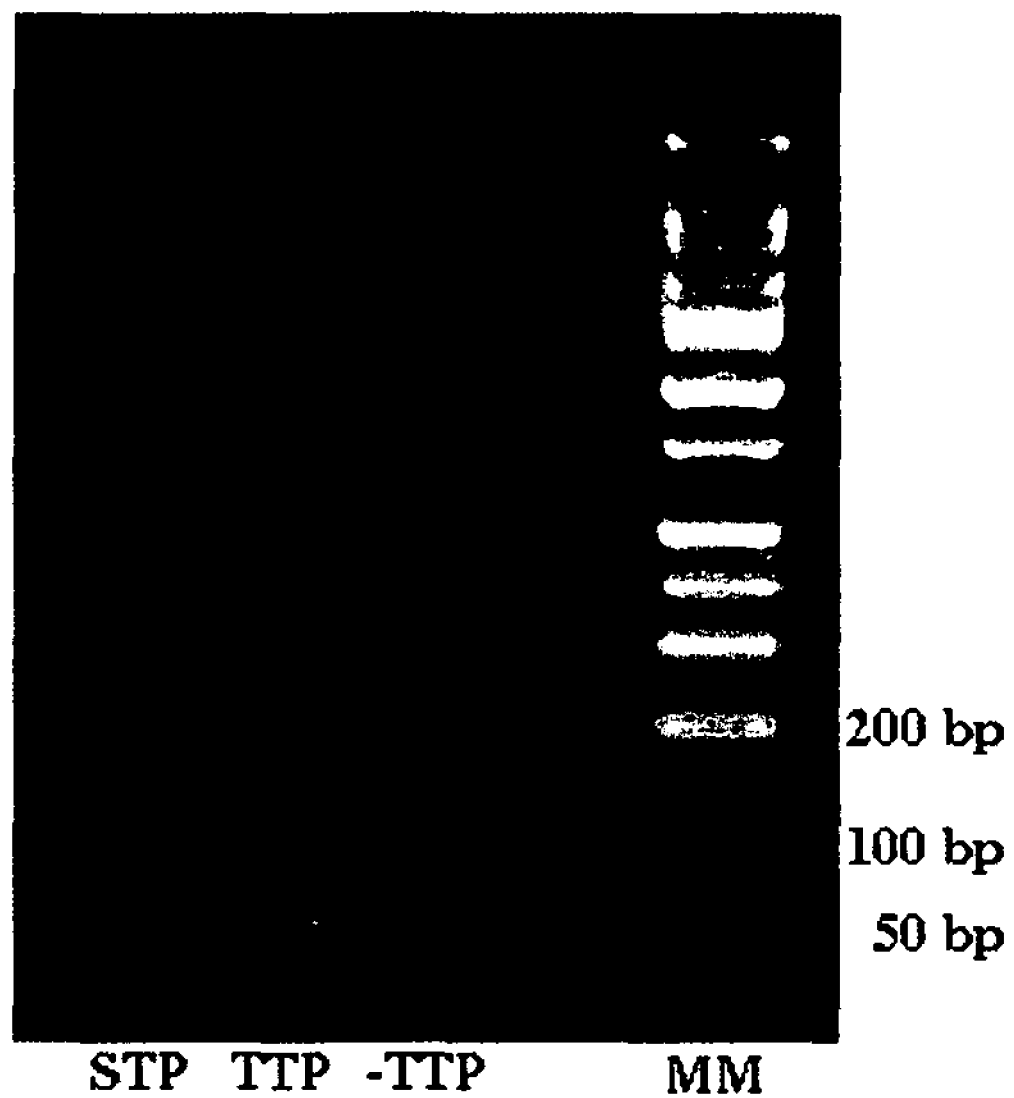
FIG. 5. PCR amplification using 2-thioTTP. The use of 2-thioTTP as a substrate for PCR was tested by performing 30 rounds of PCR in the presence of dATP, dCTP, dGTP, and either TTP, 2-thioTTP, or no thymidine analog. Following separation on a 2% agarose gel, it was observed that the reaction containing no thymidine analog produced no product (-TTP), while both TTP and 2-thioTTP (STP) containing reactions yielded similar amounts of product. MM indicates a molecular weight marker.

As seen in FIG. 5, the PCRs with TTP and 2-thioTTP generated comparable amounts of product. This result shows that 2-thioTTP is not only a satisfactory substrate for a polymerase, but can, in fact, be used as a substitute for TTP with little affect on the yield of products.

To analyze the products of a polymerase chain reaction with isoC, isoG, thioT, A, G, and C, amplification of the nonstandard base pair, we used the acid cleavage method of Johnson et al. [Joh04]. This method exploits the facile depyrimidinylation of isocytidine upon incubation in acid under conditions where the cleavage of the glycosyl bonds of the standard nucleotides is slow. The resulting a basic site is then cleaved with base, and the products are analyzed by PAGE. The relative amount of isoC that was remaining in a full length PCR product is estimated by the intensity of the cleavage band at the position where the isoC is expected, and normalized by the amount of full length product. These are crude estimates, as some cleavage occurs at other sites as well.

Figure 6:
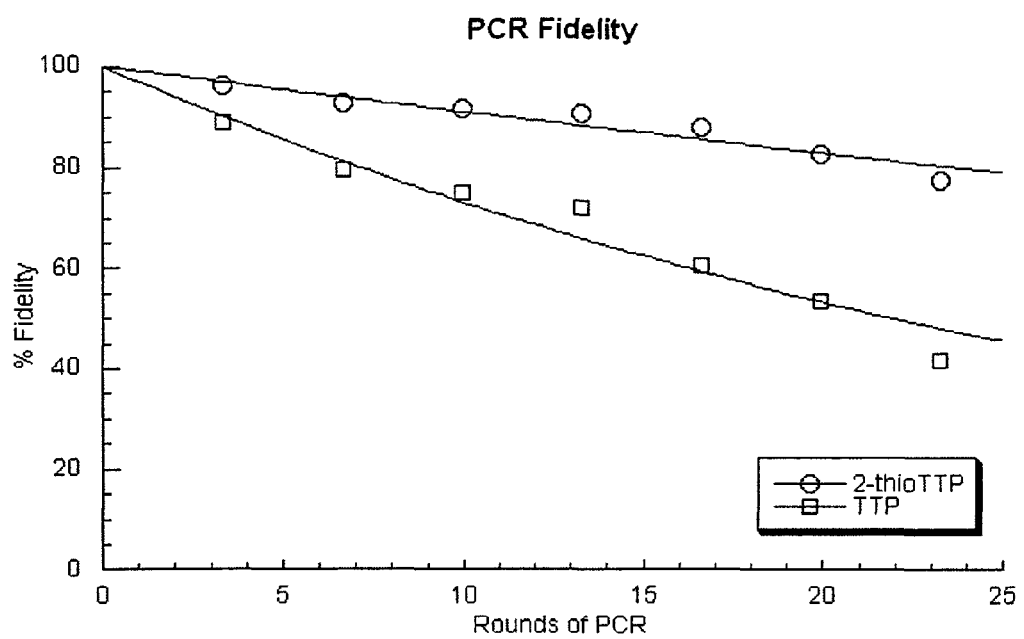
FIG. 6. Comparison of PCR fidelity using 2-thioTTP or TTP. To test the ability of 2-thioTTP to increase the fidelity of a PCR amplifying DNA containing the isoC:isoG base pair, two sets of polymerase chain reactions were conducted: one containing TTP and one containing 2-thioTTP as the thymidine analog. For reactions containing TTP or 2-thioTTP, the loss of the isoC:isoG base pair from the DNA during repeated rounds of PCR was followed by generating a series of seven PCR amplicons requiring varying amounts of amplification to extinguish available primer. Each 10-fold difference in primer/template ratio corresponds to an extra 3.32 doublings (i.e. 3.32 rounds of PCR with 'perfect' doubling) required to use all available primer. Following the cycling of each reaction for 30 rounds, reaction products were subjected to conditions that cleave the DNA at sites occupied by an isoC. The amounts of uncleaved product, containing no isoC, and cleaved product, containing isoC, were quantified following separation by PAGE. The percent fidelity, defined as the ratio of cleaved product to total product, was graphed against rounds of PCR, defined as the number of perfect doublings required to use all available primer (see Table 2 for details). To determine the fidelity-per-round of replication, f, data were fit to the equation $Y=100\times(\frac{1}{2}+f/2)^x$. Displayed are the data from each reaction set and the fitted curves. The series of amplicons containing 2-thioTTP displayed a fidelity-per-round of 98%, whereas the TTP series yielded a value of 93%.

FIG. 6 shows the disappearance of isoC in the PCR product as a function of rounds of PCR for both reactions containing TTP and those substituting 2-thioTTP. This diagram shows that isoC is lost from the PCR product much more rapidly when TTP is used than when 2-thioTTP is used. The fidelity per round was obtained by fitting the data to the theoretical curve $y=(\frac{1}{2}+f/2)^x$ (see Data Analysis section for details), where f is the fidelity per round. A PCR containing 2-thioTTP displays a fidelity-per-round of 98%. In contrast, the fidelity-per-round for PCR containing TTP is only 93%, under the conditions reported by Johnson et al. (2).

This example shows that substituting 2-thioTTP for TTP in a PCR sequence significantly increases the fidelity in a PCR amplification of an oligonucleotide containing the isoC-isoG base pair. This represents the first chemistry-enzymology combination that has both sufficient fidelity and thermostability for practical application as a 6-letter thermocycling PCR.

Direct competition experiments coupled with mercuric gel separations, as exploited here, should be generally useful in the future to assess the fidelity of incorporation of different non-standard nucleotides, when sulfur-containing nucleosides are involved. These experiments allow rapid estimation of the relative kinetic properties for competing dNTPs [Goo93][Blo93][Cre95]. This technique is preferable to the standard single nucleotide addition (primer extension) reactions or the Scintillation Proximity Assay [Lut99] previously used to distinguish those nucleotide triphosphates incorporated opposite a particular non-natural nucleoside from those that are not. This technique can also be used to optimize reaction parameters such as relative dNTP concentrations, buffers, and elongation time.

REFERENCES

[Bal04] Ball, P. (2004) Synthetic biology: Starting from scratch. *Nature* 431, 624-626

[Ben04] Benner, S. A. (2004) Understanding nucleic acids using synthetic chemistry. *Accounts Chem. Res.* 37, 784-797

[Ben05] Benner, S. A., Sismour, A. M. (2005) Synthetic biology. *Nat. Rev. Genet.* 6, 533-543

[Ben89] Benner, S. A., Moroney, S. E., Switzer, C. Y. (1989) Extending natures alphabet—Enzymatic incorporation of a new nucleotide base pair into DNA and RNA. *Abstr. Pap. Am. Chem. Soc.* 197, 174—ORGN

[Ber00] Berger, M., Ogawa, A. K., McMinn, D. L., Wu, Y. Q., Schultz, P. G., Romesberg, F. E. (2000) Stable and selective hybridization of oligonucleotides with unnatural hydrophobic bases. *Angew. Chem. Int. Edit.* 39, 2940-2942

[Blo93] Bloom, L. B., Otto, M. R., Beechem, J. M., Goodman, M. F. (1993) Influence of 5'-nearest neighbors on the insertion kinetics of the fluorescent nucleotide analog 2-aminopurine by Klenow fragment. *Biochemistry* 32, 11247-11258

[Cre95] Creighton, S., Bloom, L. B., Goodman, M. F. (1995) *DNA Replication* 262, 232-256

[Dar73] Darlix, J. L., Fromageo. P and Reich, E. (1973) Synthesis of Ribonucleic-acid containing 6-thioguanylic acid residues. *Biochemistry* 12, 914-919

[Del03] Delaney, J. C., Henderson, P. T., Helquist, S. A., Morales, J. C., Essigmann, J. M., Kool, E. T. (2003) High-fidelity in vivo replication of DNA base shape mimics without Watson-Crick hydrogen bonds. *Proc. Natl. Acad. Sci. U.S.A.* 100, 4469-4473

[Elb04a] Elbeik, T., Markowitz, N., Nassos, P., Kumar, U., Beringer, S., Haller, B., Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.* 42, 3120-3127

[Elb04b] Elbeik, T., Surtihadi, J., Destree, M., Gorlin, J., Holodniy, M., Jortani, S. A., Kuramoto, K., Ng, V., Valdes, R., Valsamakis, A. et al. (2004) Multicenter evaluation of

[Gib04] Gibbs, W. W. (2004) Synthetic life. *Sci. Am.* 290, 74-81

[Goo93] Goodman, M. F., Creighton, S., Bloom, L. B., Petruska, J. (1993) Biochemical basis of DNA-replication fidelity. *Crit. Rev. Biochem. Mol. Biol.* 28, 83-126

[Hen04] Henry, A. A., Olsen, A. G., Matsuda, S., Yu, C. Z., Geierstanger, B. H., Romesberg, F. E. (2004) Efforts to expand the genetic alphabet: Identification of a replicable unnatural DNA self-pair. *J. Am. Chem. Soc.* 126, 6923-6931

[Hik05] Hikishima, S., Minakawa, N., Kuramoto, K., Fujisawa, Y., Ogawa, M., Matsuda, A. (2005) Synthesis of 1,8-naphthyridine C-nucleosides and their base-pairing properties in oligodeoxynucleotides: Thermally stable naphthyridine:imidazopyridopyrimidine base-pairing motifs. *Angew. Chem.-Int. Edit.* 44, 596-598

[Hir04] Hirao, I., Fujiwara, T., Kimoto, M., Yokoyama, S. (2004) Unnatural base pairs between 2- and 6-substituted purines and 2-oxo(1H)pyridine for expansion of the genetic alphabet. *Bioorg. Med. Chem. Lett.* 14, 4887-4890

[Hir04] Hirao, I., Harada, Y., Kimoto, M., Mitsui, T., Fujiwara, T., Yokoyama, S. (2004) A two-unnatural-base-pair system toward the expansion of the genetic code. *J. Am. Chem. Soc.* 126, 13298-13305

[Hor95] Horlacher, J., Hottiger, M., Podust, V. N., Hubscher, U., Benner, S. A. (1995) Recognition by Viral and Cellular DNA-Polymerases of Nucleosides Bearing Bases with Nonstandard Hydrogen-Bonding Patterns. *Proc. Natl. Acad. Sci. U.S.A.* 92, 6329-6333

[Igl88] Igloi, G. L. (1988) Interaction of transfer-Rnas and of phosphorothioate-substituted nucleic-acids with an organomercurial. Probing the chemical environment of thiolated residues by affinity electrophoresis. *Biochemistry* 27, 3842-3849

[Joh04] Johnson, S. C., Sherrill, C. B., Marshall, D. J., Moser, M. J., Prudent, J. R. (2004) A third base pair for the polymerase chain reaction: inserting isoC and isoG. *Nucleic Acids Res.* 32, 1937-1941

[Kut96] Kutyavin, I. V., Rhinehart, R. L., Lukhtanov, E. A., GornVv, Meyer, R. B., Gamper, H. B. (1996) Oligonucleotides containing 2-aminoadenine and 2-thiothymine act as selectively binding complementary agents. *Biochemistry* 35, 11170-11176

[Lez67] Lezius, A. G., Scheit, K. H. (1967) Enzymatic synthesis of DNA with 4-thio-thymidine triphosphate as substitute for dTTP. *Eur. J. Biochem.* 3, 85

[Liu04] Liu, H. B., Gao, J. M., Maynard, L., Saito, Y. D., Kool, E. T. (2004) Toward a new genetic system with expanded dimensions: Size-expanded analogues of deoxyadenosine and thymidine. *J. Am. Chem. Soc.* 126, 1102-1109

[Lut99] Lutz, S., Burgstaller, P., Benner, S. A. (1999) An in vitro screening technique for DNA polymerases that can incorporate modified nucleotides. Pseudothymidine as a substrate for thermostable polymerases. *Nucleic Acids Res.* 27, 2792-2798

[Mey04] Meyer, A. S., Blandino, M., Spratt, T. E. (2004) *Escherichia coli* DNA polymerase I (Klenow fragment) uses a hydrogen-bonding fork from Arg(668) to the primer terminus and incoming deoxynucleotide triphosphate to catalyze DNA replication. *J. Biol. Chem.* 279, 33043-33046

[Mor00] Morales, J. C., Kool, E. T. (2000) Varied molecular interactions at the active sites of several DNA polymerases: Nonpolar nucleoside isosteres as probes. *J. Am. Chem. Soc.* 122, 1001-1007

[Mor97] Moran, S., Ren, R. X. F., Kool, E. T. (1997) A thymidine triphosphate shape analog lacking Watson-Crick pairing ability is replicated with high sequence selectivity. *Proc. Natl. Acad. Sci. U.S.A.* 94, 10506-10511

[Rac77] Rackwitz, H. R., Scheit, K. H. (1977) Stereochemical basis of template function. *Eur. J. Biochem.* 72, 191-200

[Rob98] Robinson, H., Gao, Y. G., Bauer, C., Roberts, C., Switzer, C., Wang, A. H. J. (1998) 2"-Deoxyisoguanosine adopts more than one tautomer to form base pairs with thymidine observed by high-resolution crystal structure analysis. *Biochemistry* 37, 10897-10905

[Sis04] Sismour, A. M., Lutz, S., Park, J. H., Lutz, M. J., Boyer, P. L., Hughes, S. H., Benner, S. A. (2004) PCR amplification of DNA containing non-standard base pairs by variants of reverse transcriptase from Human Immunodeficiency Virus-1. *Nucleic Acids Res.* 32, 728-735

[Swi89] Switzer, C., Moroney, S. E., Benner, S. A. (1989) Enzymatic Incorporation of a New Base Pair into DNA and RNA. *J. Am. Chem. Soc.* 111, 8322-8323

[Swi93] Switzer, C. Y., Moroney, S. E., Benner, S. A. (1993) Enzymatic Recognition of the Base-Pair between Isocytidine and Isoguanosine. *Biochemistry* 32, 10489-10496

[Tab95] Tabor, S., Richardson, C. C. (1995) A single residue in DNA-polymerases of the *Escherichia-coli* DNA-polymerase-I family is critical for distinguishing between deoxyribonucleotides and dideoxyribonucleotides. *Proc. Natl. Acad. Sci. U.S.A.* 92, 6339-6343

[Tae01] Tae, E. J. L., Wu, Y. Q., Xia, G., Schultz, P. G., Romesberg, F. E. (2001) Efforts toward expansion of the genetic alphabet: Replication of DNA with three base pairs. *J. Am. Chem. Soc.* 123, 7439-7440

[Vor74] Vormbroc. R, Morawiet. R and Gassen, H. G. (1974) Codon-anticodon interaction studied with trinucleoside diphosphates containing 2-thiouridine, 4-thiouridine, 2,4-dithiouridine, or 2-thiocytidine. *Biochim. Biophys. Acta* 340, 348-358

What is claimed is:

1. A process for increasing the number of copies of a portion of an initial oligonucleotide, wherein said portion incorporates one or more non-standard nucleotide units incorporating the heterocycles selected from the group consisting of isoguanine and isocytosine, wherein said process comprises:
   (a) contacting said initial oligonucleotide with an enzyme, 2-thiothymidine triphosphate, 2'-deoxyadenosine triphosphate, 2'-deoxyguanosine triphosphate, 2'-deoxycytidine triphosphate, 2'-deoxy-iso-guanosine triphosphate, and 2'-deoxy-iso-cytidine triphosphate, and derivatives of these that contain side chain modifications, and a first oligonucleotide primer that is complementary to a part of said initial oligonucleotide, and incubating the contacted mixture under conditions where said enzyme synthesizes an extension product of the first primer that is complementary to said initial oligonucleotide, wherein said first primer is selected so as to be sufficiently complementary to the initial oligonucleotide that it hybridizes therewith, such that the extension product synthesized from the first primer, when it is separated from its complement, can serve as a template for synthesis;
   (b) separating the extension products from the initial oligonucleotides on which they were synthesized to produce single-stranded molecules; and;
   (c) adding to the mixture containing the single-stranded extension products generated from steps (a) and (b) a second oligonucleotide primer that is complementary to a part of said extension products, and incubating the mixture containing the first and second primer under conditions where the enzyme synthesizes a complement of the initial oligonucleotides as well as the extension product to generate products that are extension products of both primers, wherein said second primer is selected so as to be sufficiently complementary to the extension product of the initial oligonucleotide so that it hybridizes therewith, such that the extension product synthesized from the second primer, when it is separated from its complement, can serve as a template for synthesis.

2. The process of claim 1, wherein steps (b) and (c) are repeated at least once.

3. The process of claim 1, wherein said step (b) is accomplished by denaturing.

4. The process of claim 3, wherein said denaturing is caused by heating.

5. The process of claim 1, wherein the non standard nucleotide is retained within the product to at least 90% over 5 cycles.

6. The process of claim 1, where said enzyme is a DNA polymerase.

7. The process of claim 6, where said enzyme is a Family A DNA polymerase.

8. The process of claim 7 wherein said enzyme is KlenTaq.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:

-continued

<223> OTHER INFORMATION: Synthetic

<400> SEQUENCE: 1
gcgaattaac cctcactaaa g                                          21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gcgtaatacg actcactata g                                          21

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
gcgtaatacg actcactat                                             19

<210> SEQ ID NO 4
<211> LENGTH: 36
<212> TYPE: DNA
<213> ORGANISM: Artificial Sequence
<220> FEATURE:
<221> NAME/KEY: misc_feature
<222> LOCATION: (15)..(15)
<223> OTHER INFORMATION: a nonstandard nucleotide of the instant
      invention
<220> FEATURE:
<223> OTHER INFORMATION: Synthetic

<400> SEQUENCE: 4
gtcttcgtgt cacgnccata gtgagtcgta ttacgc                          36

<210> SEQ ID NO 5
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<223> OTHER INFORMATION: Synthetic

<400> SEQUENCE: 5
gcgaattaac cctcactaaa gtacgntcgt ctatagtgag tcgtattacg c         51

<210> SEQ ID NO 6
<211> LENGTH: 51
<212> TYPE: DNA
<213> ORGANISM: Artificial Sequence
<220> FEATURE:
<223> OTHER INFORMATION: Synthetic

<400> SEQUENCE: 6
gcgaattaac cctcactaaa gtacgatcgt ctatagtgag tcgtattacg c         51